(12) United States Patent
Lovoi et al.

(10) Patent No.: US 7,253,716 B2
(45) Date of Patent: Aug. 7, 2007

(54) TRACKABLE PILLS WITH ELECTRONIC ID TAGS

(75) Inventors: Paul A. Lovoi, Saratoga, CA (US); Teri E. Judelson, Saratoga, CA (US); Anthony G. Jennetti, Sunnyvale, CA (US); Bernard Baron, Mountain View, CA (US)

(73) Assignee: Tagent Corporation, Sunnyvale, CA (US)

( * ) Notice: Subject to any disclaimer, the term of this patent is extended or adjusted under 35 U.S.C. 154(b) by 208 days.

(21) Appl. No.: 10/993,199

(22) Filed: Nov. 19, 2004

(65) Prior Publication Data

US 2006/0061472 A1 Mar. 23, 2006

Related U.S. Application Data

(63) Continuation-in-part of application No. 10/919,800, filed on Aug. 17, 2004.

(51) Int. Cl.
*H04Q 1/00* (2006.01)
(52) U.S. Cl. .................. 340/10.1; 340/573.1; 604/362
(58) Field of Classification Search ............. 340/573.1, 340/10.1; 604/362, 59, 60
See application file for complete search history.

(56) References Cited

U.S. PATENT DOCUMENTS

| 6,366,206 | B1 * | 4/2002 | Ishikawa et al. ......... 340/573.1 |
| 6,480,699 | B1 | 11/2002 | Lovoi |
| 2002/0161607 | A1 | 10/2002 | Subich |
| 2003/0127508 | A1 | 7/2003 | Jones |
| 2003/0132301 | A1 * | 7/2003 | Selker ..................... 340/572.1 |
| 2004/0032330 | A1 | 2/2004 | Hoffman |
| 2005/0285732 | A1 * | 12/2005 | Sengupta et al. ...... 340/539.12 |

* cited by examiner

Primary Examiner—Brian Zimmerman
(74) Attorney, Agent, or Firm—Thomas M. Freiburger

(57) ABSTRACT

A medical pill intended for human or animal consumption includes an RF ID tag in or on the pill. The tag will respond to a nearby reader, the tag itself being without a battery or other constant power supply, capturing power from the reader's transmitted signal and storing a portion of that power in a power supply. An antenna for the RF ID tag may be integral with the tag or it may be transferred to the pill using conductive materials in the pill's coating, filler or binding agents, embedded within the pill, or printed onto the pill. If separate from the tag the antenna is electromagnetically coupled to the tag which has a small onboard antenna. The RF ID tag of each pill has data that are transmitted when the tag is interrogated by a signal from a reader. Incorporation of an ingestable ID tag is possible because of the tag's very small size compatible with ingestion and because the tag can contain an antenna within the pill that allows the tag to be read at a substantial distance. Several different methods for deactivating the RF ID tag after ingestion or use of the pill are disclosed. Medicaments other than oral pills can also have the ID tags.

18 Claims, 6 Drawing Sheets

(a) Uni-Directional, Ellipsoid pill (b) Bi-Directional, Ellipsoid pill

Note: Arrow show direction of radiation.

(c) Omni-Directional, Spherical pill

TRACKABLE PILLS WITH ELECTRONIC ID TAGS

BACKGROUND OF THE INVENTION

This application is a continuation-in-part of application Ser. No. 10/919,800, filed Aug. 17, 2004.

The invention concerns authentication and tracking of medical pills (including pills that dissolve under the tongue or under the skin), or external medications such as skin patches, or implantable medicaments (all sometimes referred to herein as biomedical dosage units), using an embedded or attached radio frequency identification (RF ID) tag which is very small in size, on the order of about one millimeter, with no onboard battery or other constant power supply.

U.S. Pat. No. 6,480,699 describes a radio frequency identification (RF ID) tag sufficiently small to be incorporated very small within objects, even paper money. The RF ID tag includes an onboard antenna, preferably part of the same integrated circuit platform with the tag electronics. The tag acts is a transponder using the power of an interrogating signal to collect and store energy for use in transmitting a responding signal which is preferably unique to the particular tag.

The above described U.S. Pat. No. 6,480,699 mentions a number of applications for the miniature RF ID tag, which may be less than 1 mm in plane dimensions, and may be less than 0.5 mm in thickness.

In the pharmaceutical industry, there is a need for a system to accurately track pills (or other biomedical dosage units), not necessarily by a code unique to each individual pill, but by a code applied to each different type of pill. A corollary is to authenticate pills to prevent counterfeiting helping grey-market importing and other measures taken in the market place to sidestep marketing path intended by the proprietary manufacturer. Going even further, each batch of a certain pharmaceutical pill could advantageously have a unique identifier, so that the batch could be tracked electronically from manufacture until retail sale or even beyond, and each individual pill can even carry a unique identifier different from all other similar pills, useful for counting pills, in or out of a container.

There is a need to track, trace and authenticate pharmaceuticals which are in easily counterfeited, diverted and otherwise alterable forms such as pills, tablets, capsules, implantable medicaments, skin patches and other unit dosages. On Feb. 25, 2004, the Food and Drug Administration (FDA) published a final rule entitled, "Bar Code Label Requirements for Human Drug Products and Biological Products". Their objective was to improve patient safety in the hospital setting by reducing medication errors. The means to their objective was to require "bar codes" on most prescription drugs and on certain over-the-counter drugs. Bar codes are symbols consisting of parallel lines and spaces and are commonly seen on most consumer goods. In retail settings, bar codes identify the specific product and allow software to link the product to price and other sales-and inventory-related information. FDA's bar code rules uses bar codes to address an important public health concern— medication errors associated with drug products. Concurrent with this was an FDA mandate to curtail the number of counterfeit drugs by also using bar code technology. Bar coding is however, highly inaccurate, subject to humidity, and climate conditions, unable to be utilized if out of the line of sight to the reader and unable to effectively be useful on single unit dosages. Replacement of bar coding with RF ID in medical applications is not new, but the use of a small and powerful enough, all-in-one tag on or within the pill, capsule, tablet or dosage is exclusive to this invention and meets both FDA objectives.

It is an object of this invention to provide a system which makes such authentication and tracking of medical pills possible, efficient and cost effective.

SUMMARY OF THE INVENTION

A medical pill or the medicament intended for human or animal consumption or use includes an RF ID tag in or on the pill. The invention also applies to external medications such as skin patches, or other medications, especially (but not necessarily) prescription medications, including implantable medicaments. The general principle of the invention can apply to oral liquids, eye drops, creams and suppositories. The tag can be on a container in some instances. This tag will respond to a reader which may be one or several meters away, the tag itself being without a battery or other constant power supply. An antenna for the RF ID tag is integral with the tag when inserted in or attached to the pill, and it may be transferred to the pill by coupling to conductive materials in the pill's coating, filler or binding agents, embedded within the pill, or printed onto the pill, to form an enhanced antenna or the pill itself can form a radiating structure as part of the antenna. The antenna if separate from the tag is electromagnetically (e.g. capacitively) coupled to the tag which is inside the pill, under the coating of the pill, or on the surface of the pill. The RF ID tag of each pill has data that are transmitted when the tag is interrogated by a signal sent from a reader. The incorporation of an ingestable ID tag is possible because of the ability of the tag to exist in a size compatible with ingestion, as well as to contain an antenna within the pill that allows the ID tag to be read at a substantial distance. The tag captures power from the reader's transmitted signal and stores a portion of that power in a power supply of the integrated circuit. Several different methods for deactivating the RF ID tag after ingestion of the pill, for privacy and other reasons, are disclosed.

Most pills comprise solid compressed powders which would be suitable for sustaining a tag with an integral or coupled antenna. Microchips do not interfere with the bio-availability of active pharmaceutical ingredients. Pills are manufactured to process steps that include blending, granulating, compressing, drying, assuring uniformity of active ingredients in dosage form, branding, coating, finishing and packaging. The final stages of branding, coating, finishing and counting are logical and likely insertion point choices for an RF ID tag according to the invention. Pill formulations generally include fillers, which give the pill volume and commonly comprise lactose, micro crystalline cellulose, cornstarch, sugars (including sucrose, mannitol, sorbitol, fructose, and dextrose), whey and yeast, binders such as povidone, xanthan gum and Carbopol (an acrylic like resin) which stick components together when ingredients are compressed to form the pill, and disintegrants such as crospovidone, croscarmellose sodium and gellan gum, which facilitate the break-up of the tablet in the stomach. Coatings prevent the tablet from dissolving too soon, and also mask the tasting or smelling of the active ingredients. Other ingredients, such as lubricants, colorants, flavors (especially in chewable tablets) and plasticizers, may also be present in a pill.

The principle of RF ID is known from the above U.S. Pat. No. 6,480,699 as well as other prior disclosures. However, with this invention a proprietary tag having dimensions approximately 1 to 4 mm in planar dimensions (or smaller), and very small thickness, will fit in or on approximately 98% of all existing medical pill dimensions. A receiving and transmitting antenna is either placed on or embedded within the pill. The purpose of the antenna is to receive the reader signal which powers the tag's chip and to re-transmit data back to the tag's reader, identifying the pill. The antenna can be shaped suitably to be biocompatible and to adhere to the tablet or capsule shape and size. In a specific embodiment, the pill itself helps form the antenna.

If desired, electromagnetic or parasitic coupling can be used to couple to or excite antennas or electromagnetic structures printed on the pill. These new structures could be from conducting ink used for pill branding or printed identification.

If the tag is to be turned off and prevented from further transmissions prior to ingestion, such as for privacy reasons, a reactive cancellation device may be used which cancels out the reactance of the coupling device. In this method the material of the pill itself is part of the circuit of the antenna. It actually helps match the antenna so when the pill dissolves in the body, it will degrade in performance significantly. In addition, because the body contains so much water, the tag device will not transmit significant energy out of the body, especially with the reduced performance antenna. For any of the embodiments an external deactivator could be used, usable at a pharmacy where the medicine is purchased, or consumers/patients could have a deactivator in or near the home medicine cabinet. A pre-programmed clock could be included in the tag to deactivate at a certain time, if desired. Other methods of turning off the tag are described as well.

The inclusion of miniaturized RF ID systemized single unit medical dosage (pill) has the following benefits:

(1) insertion of the miniature-sized RF ID tag does not change the pill's characteristics;

(2) the tag leaves the active ingredients of the pill unaltered;

(3) the tag presents minimal chance of mechanical or chemical hazard from ingestion due to biocompatible design constraints;

(4) only negligible amounts of silica are absorbed by the patient (single dose of residual tag material (per 3 mm tag) has a daily tolerance threshold of 50 pills per day per individual, requiring consumption of over 18,000 pills per year to be statistically noticed), because of the protective characteristics of smooth muscle cells of the alimentary and elimination systems and of the digestive process itself.

(5) Electrical hazard from ingesting an RF ID tag emitting at a low operating frequency is well below the threshold of other FDA approved insertable electrical emitting devices such as pacemakers.

(6) Privacy hazards are eliminated by the ability to cancel or deactivate the tag, electrically, by an external cancelling device, at body temperature, pH, by liquid dissolution of components or other physically verifiable parameters.

In a specific embodiment of the invention, the RF ID tag has an antenna formed by a metal or semiconductor trace on or near the surface of a pill. The metalized trace may be on the opposite side of the pill from the tag itself, with the tag and trace in prescribed alignment so as to establish a strong capacitive coupling between the small antenna onboard the tag and the metalized trace. The current in the tag dipole excites currents in the long metal trace on the other side of the pill, acting as an antenna coupled to the tag circuitry. The effect is to form an extended aperture radiating system, increasing the size of the tag antenna using the thin metal trace. The electrical properties of the metal trace create an antenna with properties different from that of the isolated RF ID tag. The aperture of the tag is changed to include the larger structure of the pill trace.

In a further specific embodiment, the pill does not include a metalized trace but the pill itself forms an extended aperture radiating system. The size of the tag antenna is increased by the addition of the pill, the electrical properties of which create an antenna with properties differing from the isolated RF ID tag. In some instances the radiation from the tag is enhanced and made directional. In all cases and at any frequency, the aperture of the tag is changed to include the larger structure of the pill.

It is therefore among of the objects of the invention to provide a reliable, efficient and economical system for electronically and automatically authenticating and tracking pharmaceutical dosages and medicaments, without adverse effects on patients and avoiding any privacy concerns. These and other objects, advantages and features of the invention will be apparent from the following description of preferred embodiments, considered along with the drawings.

DESCRIPTION OF PREFERRED EMBODIMENTS

Figure 1:
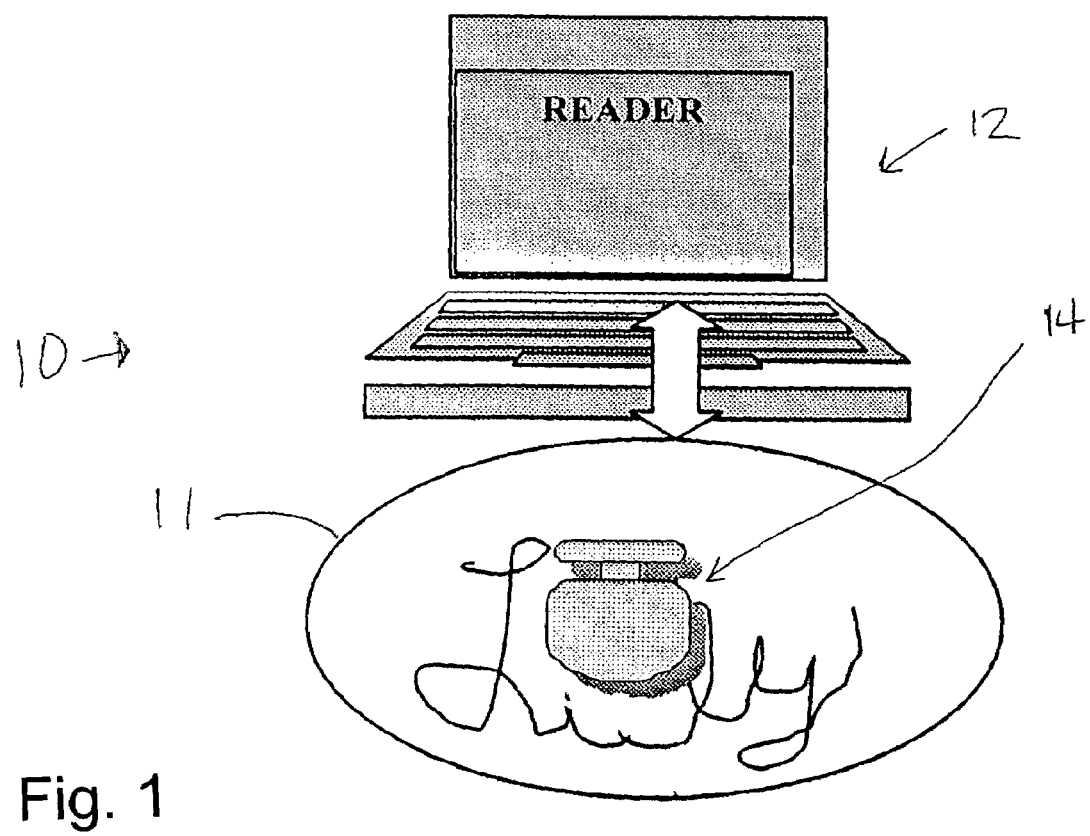
FIG. 1 is a schematic view showing a pharmaceutical pill in tablet form and indicating an RF ID tag incorporated in the pill and showing a reader to read a return signal from the tag.

In the drawings, FIG. 1 schematically indicates a pill verification and tracking system 10, including a pharmaceutical dosage, specifically a pill 11, and a reader 12. The reader sends out an interrogating signal, generally as explained in the above mentioned U.S. Pat. No. 6,480,699, which is incorporated herein by references, and in the above referenced co-pending application. A radio frequency ID tag device 14 is incorporated in the pill 11 either on the surface of the pill or inside the pill. The tag also is constructed generally in accordance with the disclosure of the above patent and co-pending application. In FIG. 1, the pill 11 is shown as a tablet, while in FIG. 2 the pill is a capsule 11a. Indicia 13 may be included on the pill 11 (or the pill 11a) to identify the manufacturer or the drug name. The interrogating signal from the reader 12 provides power for the RF ID tag 14 collected by an antenna and a power supply on the tag. If the tag is within approximately 1 or 2 meters of the reader 12, sufficient power is captured and stored by the tag to power the tag's onboard circuitry to produce and transmit a responsive signal from the tag, capable of being read by the reader 12.

In the preferred embodiments the RF ID tag 14 may be about 1 to 4 mm in size, as to length and width (although it could be smaller), and is about 0.5 mm or less in thickness. More preferably, particularly for smaller pills, the tag is about 1 to 2 mm in length and width dimensions, most preferably no larger than about 1 mm square. The tag is thus quite small compared to the size of the pill, the pill being typically about ¼ inch (6-7 mm) to about 1 inch (25 mm) in length.

The tag 14 is shown schematically on the pill in FIG. 1. Depending on the composition of the pill and other factors, it may be embedded into a tablet before the tablet is dried and hardened, pressed into the surface; or it may be contained deeper within the tablet. If desired the tag may simply be adhered permanently to the surface of a tablet, or of a capsule 11a, in a manner that will readily reveal tampering or removal, in such a way that the tag would be destroyed if removed. The tag's antenna may be integral with the tag, or it may be separate and transferred to the pill itself by using conductive materials in the pill's coating, filler or binding agents and/or embedded within the pill. If separate, the antenna is electromagnetically coupled to the RF ID tag inside of, under the sealant or coating of, or on the surface of the pill. Each pill has its own antenna and RF ID tag.

As noted above, the described invention as applied to oral pills is made possible by the ability of the RF ID tag to exist in a size compatible with ingestion or intake by humans or animals, as well as to contain an antenna within the pill that allows the RF ID tag to be read at a longer range, increasing the workable distance of the tag.

Figure 2:
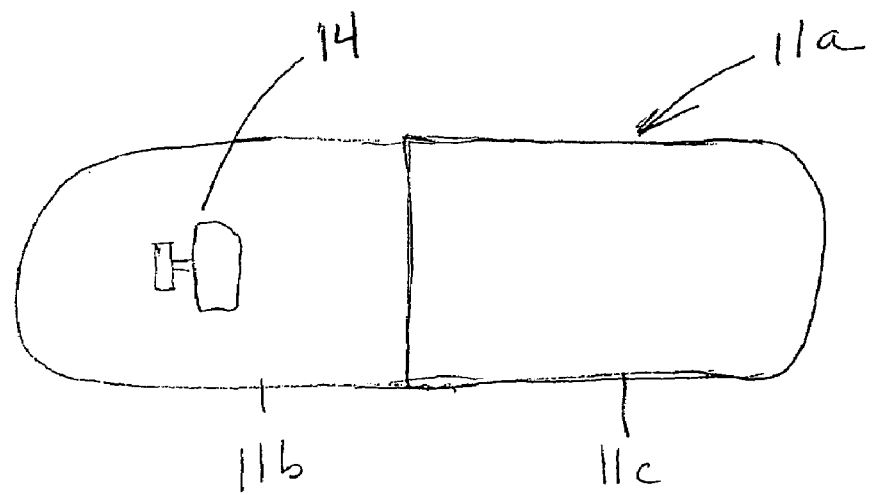
FIG. 2 is a view showing the pharmaceutical pill in the form of a capsule, again showing the incorporation of an RF ID tag.

FIG. 2 indicates a capsule 11a, with connected shells 11b and 11c, with an RF ID tag 14 in accordance with the invention. In a capsule, the tag 14 can simply be contained within the powder or granules inside the capsule, or it can be attached to the inner surface of one of the capsule shells, or to the outer surface by adhesion or gel embedding, for example.

Figure 3:
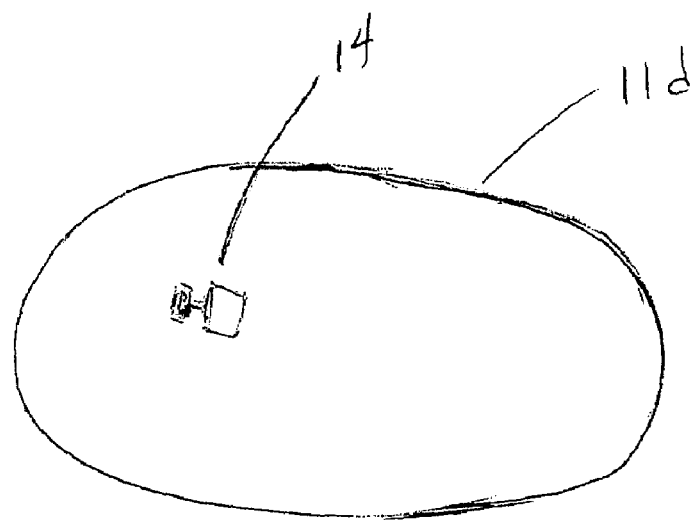
FIG. 3 is a detail view showing the pill of FIG. 1 and indicating the tag substantially to scale on or in the pill.

FIG. 3 shows a pill 11d, which can be considered either a tablet or a capsule or a gel type tablet or capsule, and showing the tag 14 substantially to scale, for a pill having a length dimension between about ½ inch and 1 inch. If the pill 11d is ½ inch in length, then the tag 14 has a maximum dimension of about 1.5 mm. If the pill 11d is 1 inch in length, then the tag has a dimension of about 3 mm. The tag may actually be smaller, but FIG. 3 gives an idea roughly of the proportion of the tag compared to the pill.

For tablets, affixing of the tag can be by spray affixing, autokinetic coating, continuous coating, electrostatic coating, by radiant heat, or by other methods.

Figure 4:
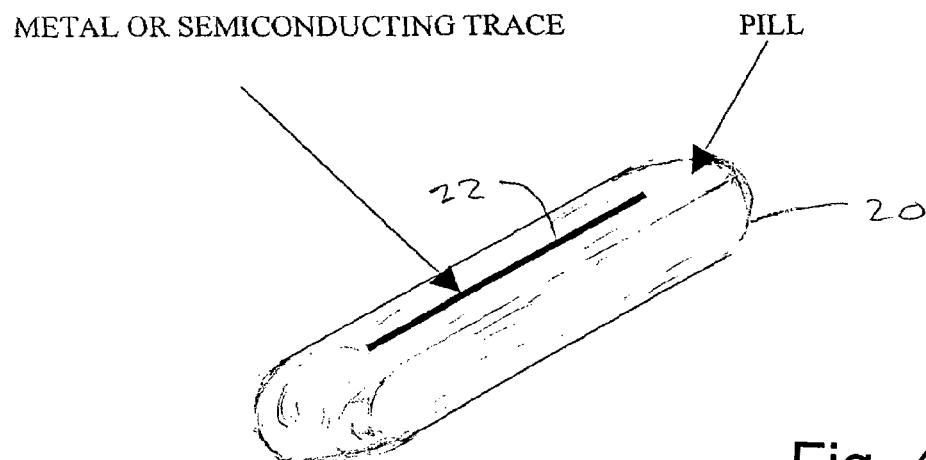
FIG. 4 is a schematic view in perspective showing a pill with a deposited metalized trace on its surface to form an enhanced antenna.

FIG. 4 shows another embodiment of a medical pill 20, indicated schematically, with a metal or semiconductive trace 22 on one surface. The trace can be placed on the pill by printing or other techniques used to place indicia on the surface of a pill in the pharmaceutical industry. In this case the metalized or semiconductive trace 22 acts as an antenna for the tag contained in or on the pill, the tag not shown in FIG. 4. The antenna 22 is capacitively coupled to the tag and as discussed below, may be directly adjacent to the tag or spaced away from the tag.

Figure 5:
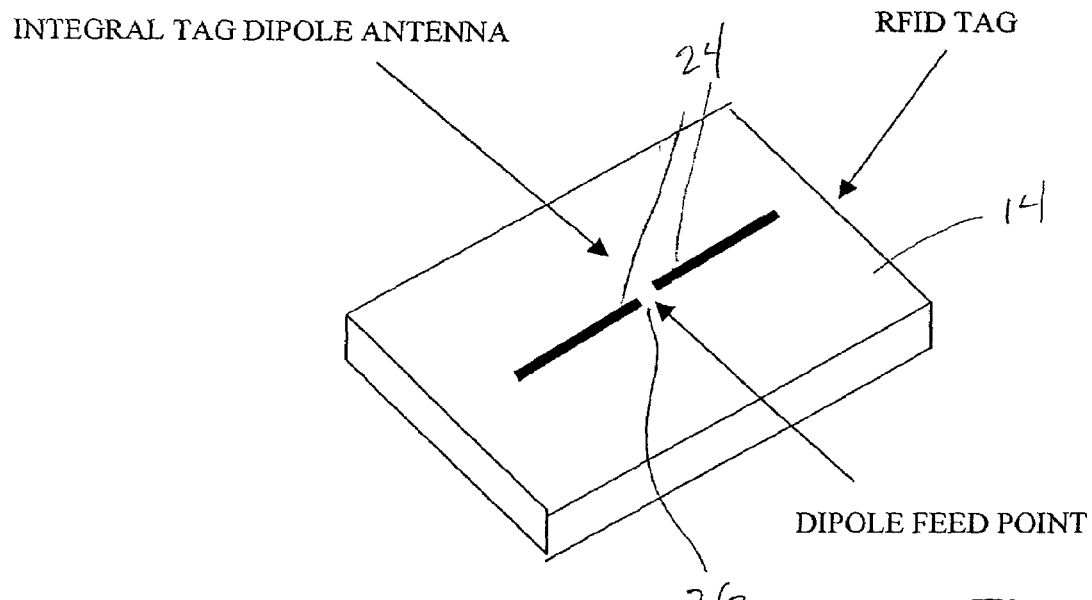
FIG. 5 is a schematic view in perspective showing a RF ID tag, also to be included in the pill of FIG. 5, with an integral tag antenna in a capacitively coupled relationship with the trace shown in FIG. 5.

FIG. 5 shows an RF ID tag 14 schematically. This tag 14 has an integral dipole antenna 24, known as a short dipole. Other types of antennas could be used as well. The transmit and receive circuitry of the tag 14 is attached to the dipole feed point, shown at 26.

Figure 6:
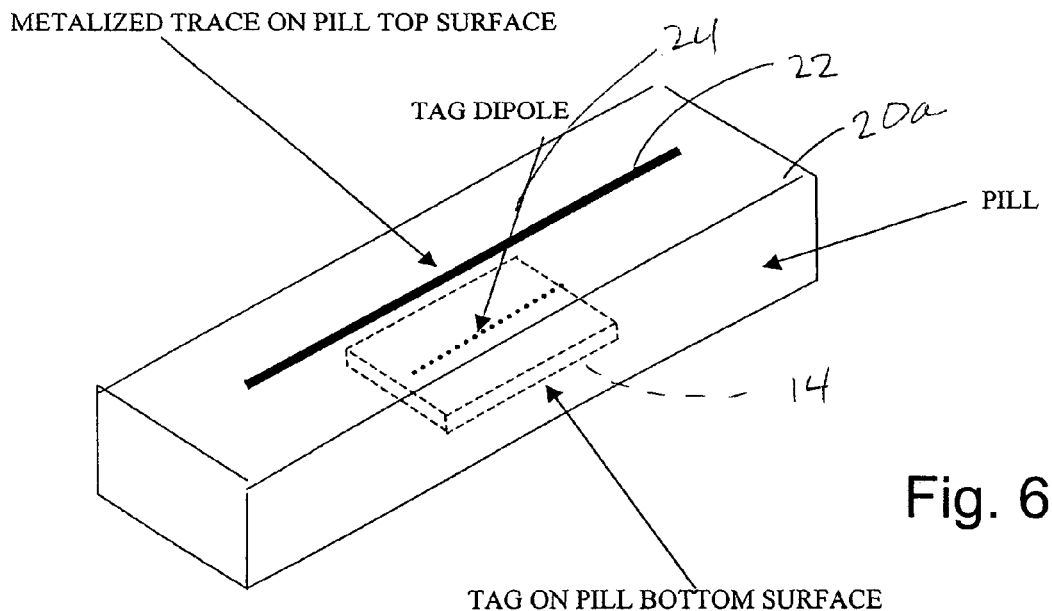
FIG. 6 is another schematic view in perspective, showing one embodiment of the pill with the conductive trace and the RF ID tag, in this case spaced apart, as on opposite sides of the pill.

There are two basic methods of exciting the deposited trace 22 on the pill of FIG. 4, with the tag of FIG. 5. One method is to place the tag on the opposite of the pill from the trace. For the tag of FIG. 5, the tag is installed so that the dipole is roughly in line with the metal or conductive trace, as shown in FIG. 6. Since the pill material is dielectric, sometimes including silicon dioxide, the current in the tag dipole 24 excites current in the long metal trace 22 on the other side of the pill, and the trace acts as an antenna coupled to the tag circuitry. In the arrangement of FIG. 6 the tag 14 may be secured to the bottom surface of the pill, just inside the pill coating, or on the inside surface of a capsule shell on the opposite side of the pill, or elsewhere within the pill but spaced from the trace 22.

Figure 7:
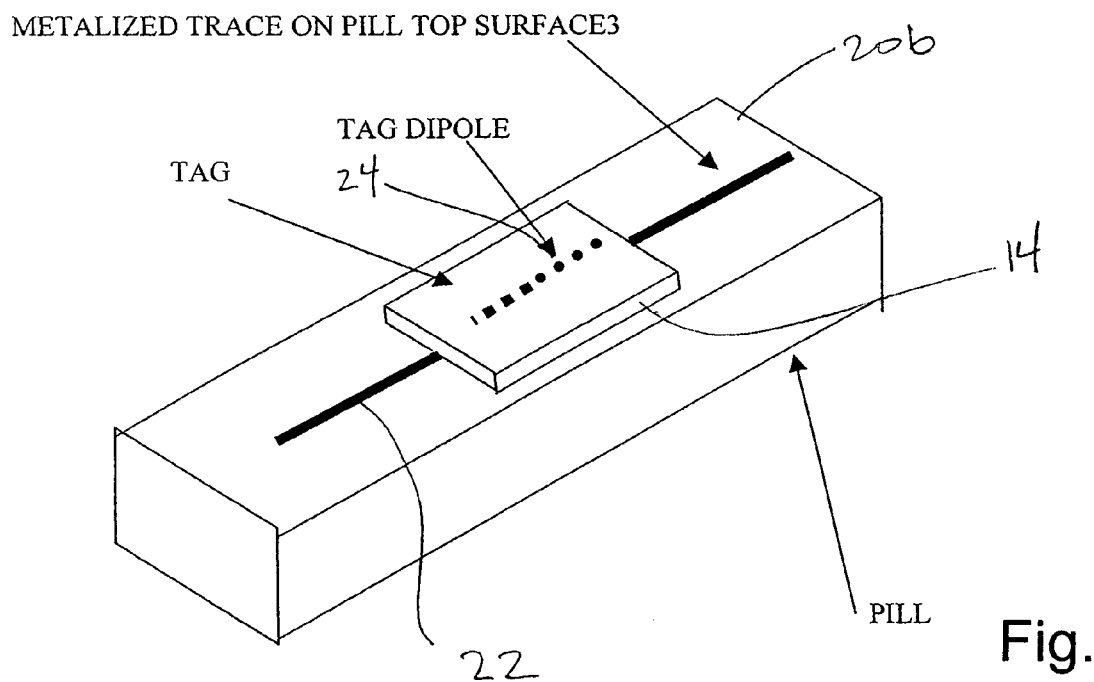
FIG. 7 is a view similar to FIG. 6, but showing an embodiment in which the conductive trace and the RF ID tag are adjacent, both on the same side of the pill.

The second method is to install the tag on the same surface as the metalized trace, such as directly on top of the trace, as shown in the pill 20b in FIG. 7. In the chip manufacturing process, a thin layer of dielectric material (between about 0.5 and 1.5 micron thick) is placed over the tag 14. This prevents direct electrical connection to the metalized trace, but allows strong electromagnetic coupling between the tag antenna 24 and the metalized trace 22. Instead of being placed directly on top of the conductive trace 22, the tag 14 could be, for example, on the inside surface of a capsule shell, directly adjacent to the trace 22 on the outside surface of the shell.

More than one antenna can be included in or on the pill if desired. A secondary antenna (whether integral with the tag or separate and coupled) can improve the probability of detection, especially if the pills are aggregated in a box or drum or other container.

FIGS. 8 through 12 relate to a different embodiment of the invention, in which the pill itself effectively forms part of the antenna of the tag device. The RF ID tag has an integral antenna and is mounted on or within a pill to form an extended aperture radiating system. The size of the tag antenna is increased by the addition of the pill. The pill electrical properties create an antenna with properties different from that of the isolated RF ID tag. In some instances, the radiation from the tag is enhanced and made directional. In all cases and at any frequency, the aperture of the tag is changed to include the larger structure of the pill. The pill and the tag constitute a radiating structure and can be considered as an entity with properties due to or arising from their combination. The electrical operation of this combination is not simple. It is characterized depending upon frequency or wavelength. This characterization is shown in Table I.

TABLE I

| Pill Size | <<λ | 0.25–5 λ | >>10 λ |
|---|---|---|---|
| Antenna Mode | Omni | Polyrod | Lens |
| Directivity | 0 dBi | 3 to 10 dBi | >>10 dBi |
| Beamwidith* | 180–360 deg | 120–52 deg | <<52 deg |
| Frequencies | <1 GHz | 3.7–73 GHz | >100 GHz |

*1 inch long ellipsoid pill

At medium wavelength frequencies there exists a directional antenna called a polyrod antenna. This antenna consists of two items:

(A) a elongated dielectric structure, such as, but not restricted to, a cylindrical rod, and (B) an exciting feed antenna positioned at one end of the dielectric structure.

The polyrod antenna is a radiating structure which radiates end-fire (in the direction of the rod) and forms a directive antenna beam. The rod is generally longer than a half wavelength although it will function as a traveling wave antenna at a quarter wavelength. The gain is proportional to the length of the rod, provided the rod is long enough to set up a traveling wave. The polyrod operates in the hybrid HE11 mode which does not have a lower cut-off frequency. It is expected that a quarter of a wavelength in length is the conventional lower limit for traveling wave operation. The dielectric loading that exists throughout the antenna can be beneficial even at yet lower frequencies.

The polyrod is usually fed with a waveguide operating in the TE11 mode. This is not a strict requirement. It can be fed with any antenna that is capable of exciting its structure. It is sometimes excited with a Yagi-Uda antenna. The feed antenna is usually uni-directional in the direction of the rod, although this, again, is not necessary. The necessary requirement is that the antenna must be close enough to couple into the dielectric. Since the HE11 mode exhibits no lower bound in cutoff frequency, the antenna can function at lower frequencies.

Figure 8:
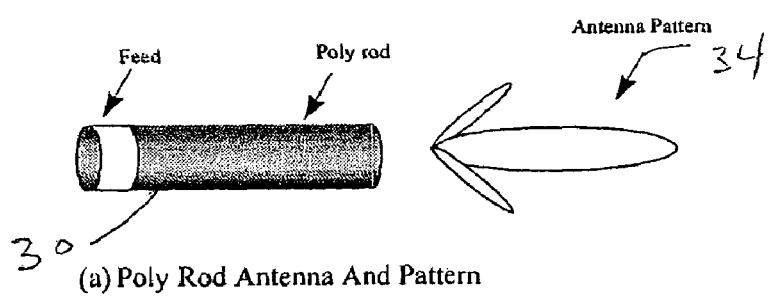
FIG. 8 schematically shows a polyrod antenna, with indication of its gain pattern.
Figure 9:
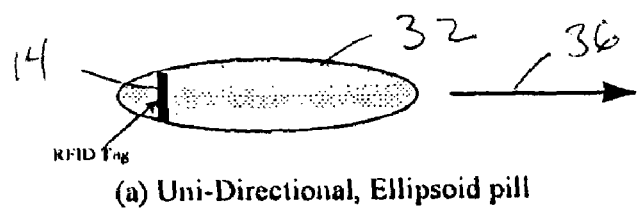
FIG. 9 shows a pharmaceutical pill of generally ellipsoid shape and with an RF ID tag near one end, for comparison with the polyrod antenna of FIG. 8.

An RF ID tag antenna embedded in the pill meets the above two requirements for an antenna. FIGS. 8 and 9 make a comparison between a polyrod antenna already shown in FIG. 8 and the ellipsoid pill 32 shown in FIG. 9. The gain pattern of the antenna is indicated at 34 in FIG. 8. For the ellipsoid pill of FIG. 9, the RF ID tag 14 is shown at or near one end of the pill. The radiation direction is indicated by the arrow 36 in FIG. 9. In the pill 32 of FIG. 9 the pill is a dielectric structure with a specific shape. The RF ID tag 14 with its onboard antenna acts as the exciting antenna.

Figure 10:
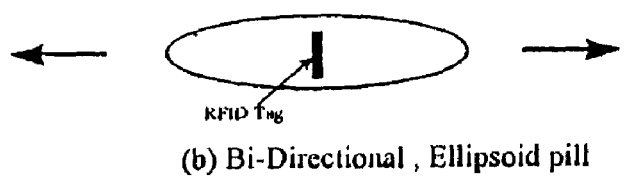
FIG. 10 a pill of similar shape, in this case with the RF ID tag placed generally centrally in the pill and showing radiation directions.
Figure 11:
FIG. 11 schematically shows a generally spherical pill with a tag located centrally and indicating omnidirectional radiation from the tag.

FIGS. 9-14 show three dispositions of dielectric antennas with an embedded RF tag. FIG. 9, as noted above, shows an ellipsoid pill 32 with a tag 14 at one of the ends, resulting in behavior as a uni-directional polyrod antenna. The tag exciter can be either uni-directional or bi-directional. The mass of the pill will tend to direct the energy along the axis of the pill even though the exciting antenna may not be uni-directional. The pill is assumed composed of a material with dielectric properties suitable to support a surface wave for the appropriate set of conditions to form a traveling-wave mode similar to the HE11 cylindrical waveguide mode, an ellipsoid hybrid mode. For analysis purposes, note that a typical upper limit on pill lengths is on the order of about 1 inch, or 25.4 mm. FIG. 10 shows a bi-directional dielectric antenna where the RF ID tag exciter is situated essentially in the center of the pill. In this case, the pill radiates a beam in both directions. Finally, there is a tag in a small pill, approximately spherical, shown in FIG. 11. The radiation will tend to be omni-directional (within a plane) for cases when the pill is not large in terms of wavelengths.

Directionality is impacted by the size of the wavelengths of the pill. At 5 Ghz, an ellipsoid pill is beginning to become distinctly directional whereas a small spherical pill will be omni-directional at this frequency. It is important to note these distinctions in the application of this invention.

There are other advantages to having an antenna inside of a pill which are a part of this invention:

1. The directionality of the end-fed ellipse-pill combination means that the pill must be pointed in the direction of the tag reader. This may be an important factor in packaging, shipping or in administration of medication dosage. The directionality will tend to minimize interference. When a directional pill is given to a patient, the pill may have to be positioned in the direction of the tag reader. This may be an advantage in enforcing discipline or quality control. For shipping and receiving, directionality may impart large advantages.

2. The dielectric surrounding the pill can act as a matching surface or transition between the RF ID tag antenna and the surrounding media. This is important if the pill is immersed in a high dielectric constant medium such as the human body, cell tissue or packaging material or packaging systems with higher dielectric constant.

3. The dielectric constant of the pill will produce a higher flux density, $D=\epsilon_r E$, where D is the flux density, E is the field in units of volts/meter, and $\epsilon_r$ is the relative dielectric constant of the pill material. This increase in flux density can be beneficial to the antenna. This factor may improve the performance when the pill is small in terms of wavelengths, and is very important for that situation and the feature can be very useful, as a different mode from the polyrod mode of operation.

As noted above, the RF ID tag can also be applied to other medications, such as external skin patches, implantable medicaments, pills that dissolve under the skin or under the tongue; or on containers for liquids or salves, suppositories, etc. In the case of skin patches, for example, the medication goes into the body but the ID tag does not, so that deactivation mechanisms based on dissolving or other ingestion phenomena generally do not apply. Deactivation can be via an external deactivator (such as using RF), or the tag can include a pre-programmed clock, as noted above.

The invention also encompasses the carrying of additional information on a tag of a pharmaceutical, or on an additional tag on the same pill or other medicament. Product information, dosage formations or other information can be carried.

This technology can be used on fast dissolve, modified release, dose loading and drug delivery tablet types. Different release profiles are possible; for example, a fast release coat around a modified release core, enabling separation of the tag and use of a coating that can contain a second drug product.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A trackable, authenticatable medical pill, comprising:
a pill of substantially conventional configuration, size, construction and chemistry, essentially not larger than about 3 cm in length and about 1 cm in diameter, a radio frequency ID tag on or in the pill, including an antenna and an integrated circuit connected to the antenna, and the integrated circuit including a power supply for storing a portion of energy received by the antenna from a separate reader device that sends out an RF power signal for interrogating a plurality of similar ID tags, a processor circuit receiving power from the power supply and for originating a response to the power signal from a reader device, and a transmitter connected to the processor circuit for transmitting a response signal from the pill to identify or authenticate the pill, the transmitted signal being sent via the antenna, wherein the medical pill comprises a capsule containing the medication, and wherein the antenna is integrated with a wall of the capsule, and wherein the antenna includes a conductive trace on the wall of the capsule, spaced away from and electromagnetically coupled to the RF ID tag, whereby medical pills with the ID tags can be verified for authenticity and/or tracked until medication of the pill is ingested or absorbed by a patient.

2. The apparatus of claim 1, wherein the antenna includes a small, integral onboard antenna on the tag which is coupled electromagnetically to the conductive trace.

3. A trackable, authenticatable medical pill, comprising:
a pill of substantially conventional configuration, size, construction and chemistry, essentially not larger than about 3 cm in length and about 1 cm in diameter, a radio frequency ID tag on or in the pill, including an antenna and an integrated circuit connected to the antenna, and the integrated circuit including a power supply for storing a portion of energy received by the antenna from a separate reader device that sends out an RF power signal for interrogating a plurality of similar ID tags, a processor circuit receiving power from the power supply and for originating a response to the power signal from a reader device, and a transmitter connected to the processor circuit for transmitting a response signal from the pill to identify or authenticate the pill, the transmitted signal being sent via the antenna, and including a means for rendering the tag inactive and non-readable after use by a patient, whereby medical pills with the ID tags can be verified for authenticity and/or tracked until medication of the pill is ingested or absorbed by a patient.

4. The apparatus of claim 3, wherein said means for rendering the tag inactive comprises a means for destruction of the antenna after ingestion.

5. The apparatus of claim 4, wherein the means for destruction of the antenna comprises the antenna including soluble material in the structure of the pill, whereby the antenna is destroyed by dissolving after ingestion.

6. The apparatus of claim 3, wherein said means for rendering the tag inactive comprises a means for degradation of the tag by gastric PH to which the tag is exposed inside the patient after ingestion.

7. A trackable, authenticatable medical pill, comprising:
a pill of substantially conventional configuration, size, construction and chemistry, essentially not larger than about 3 cm in length and about 1 cm in diameter, a radio frequency ID tag on or in the pill, including an antenna and an integrated circuit connected to the antenna, and the integrated circuit including a power supply for storing a portion of energy received by the antenna from a separate reader device that sends out an RF power signal for interrogating a plurality of similar ID tags, a processor circuit receiving power from the power supply and for originating a response to the power signal from a reader device, and a transmitter connected to the processor circuit for transmitting a response signal from the pill to identify or authenticate the pill, the transmitted signal being sent via the antenna, and wherein the antenna comprises a small onboard integral antenna on the tag as well as a conductive trace on or near the surface of the pill and much longer than the onboard antenna of the ID tag, and wherein the radio frequency ID tag is located at a spaced location from the conductive trace, the onboard antenna on the tag being in electromagnetically coupled relationship with the conductive trace such that the conductive trace enhances the tag's antenna producing an increase in radiation efficiency for tag transmission as well as an increase in power received from the power signal of a reader device, whereby medical pills with the ID tags can be verified for authenticity and/or tracked until medication of the pill is ingested or absorbed by a patient.

8. The apparatus of claim 7, wherein the conductive trace comprises a metalized trace.

9. The apparatus of claim 7, wherein the conductive trace is generally at one side of the pill and the tag is generally at an opposite side of the pill.

10. The apparatus of claim 7, wherein the conductive trace comprises a metalized trace deposited on an exterior surface of the pill.

11. The apparatus of claim 7, wherein the pill is about 0.5 to 0.8 inch in length, and wherein the RF ID tag is about 0.04 inch square and no more than about 0.02 inch thick.

12. The apparatus of claim 7, wherein the tag and the conductive trace are located adjacent to one another, at one surface of the pill.

13. The apparatus of claim 12, wherein the conductive trace is on the surface of the pill and the RF ID tag is placed directly on top of the trace, the tag having a thin layer of dielectric material over its surface preventing direct electrical connection between the trace and the tag.

14. A trackable, authenticatable medical pill, comprising:
a pill of substantially conventional configuration, size, construction and chemistry, essentially not larger than about 3 cm in length and about 1 cm in diameter, a radio frequency ID tag on or in the pill, including an antenna and an integrated circuit connected to the antenna, and the integrated circuit including a power supply for storing a portion of energy received by the antenna from a separate reader device that sends out an RF power signal for interrogating a plurality of similar ID tags, a processor circuit receiving power from the power supply and for originating a response to the power signal from a reader device, and a transmitter connected to the processor circuit for transmitting a response signal from the pill to identify or authenticate the pill, the transmitted signal being sent via the antenna, and wherein the radio frequency ID tag is positioned in the pill such as to form an extended aperture radiating system, the pill itself forming a part of the antenna for the tag and the size of the tag antenna being increased by the pill, the pill and tag in combination forming a radiating structure, whereby medical pills with the ID tags can be verified for authenticity and/or tracked until medication of the pill is ingested or absorbed by a patient.

15. The apparatus of claim 14, wherein the tag is positioned near one end of an elongated pill such that radiation from the pill and tag is essentially uni-directional and essentially in a polyrod mode of operation.

16. The apparatus of claim 14, wherein the tag is positioned at or near the middle of an elongated pill such that the tag and pill emit radiation essentially bi-directionally.

17. The apparatus of claim 14, wherein the pill is smaller than about one-quarter of the wavelength of RF radiation emitted from the tag, and wherein radiation from the tag and pill combination is essentially omni-directional within a plane.

18. The apparatus of claim 17, wherein the pill is approximately spherical.

* * * * *